US012116566B2

United States Patent
Guarnieri et al.

(10) Patent No.: US 12,116,566 B2
(45) Date of Patent: Oct. 15, 2024

(54) PHOTOSYNTHETIC PROTEIN SECRETION PLATFORM

(71) Applicant: Alliance for Sustainable Energy, LLC, Golden, CO (US)

(72) Inventors: Michael T. Guarnieri, Denver, CO (US); Lukas Royce Dahlin, Golden, CO (US); Marcus Salvatore Bray, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/666,345

(22) Filed: Feb. 7, 2022

(65) Prior Publication Data
US 2022/0251500 A1 Aug. 11, 2022

Related U.S. Application Data

(60) Provisional application No. 63/146,469, filed on Feb. 5, 2021.

(51) Int. Cl.
| | | |
|---|---|---|
| *C12N 1/12* | (2006.01) | |
| *C07K 14/405* | (2006.01) | |
| *C07K 14/435* | (2006.01) | |
| *C12P 21/02* | (2006.01) | |

(52) U.S. Cl.
CPC .......... *C12N 1/12* (2013.01); *C07K 14/43595* (2013.01)

(58) Field of Classification Search
CPC ................ C12N 1/12; C07K 14/43595; C07K 14/405; C07K 2319/02; C12R 2001/89; C12P 21/02
See application file for complete search history.

(56) References Cited

FOREIGN PATENT DOCUMENTS

WO   WO 2008/142034   * 11/2008   ............. C12N 15/82

OTHER PUBLICATIONS

Dahlin, L. R., Gerritsen, A. T., Henard, C. A., Van Wychen, S., Linger, J. G., Kunde, Y., . . . & Guarnieri, M. T. (2019). Development of a high-productivity, halophilic, thermotolerant microalga Picochlorum renovo. Communications biology, 2(1), 388. (Year: 2019).*

Molino, J. V. D., de Carvalho, J. C. M., & Mayfield, S. P. (2018). Comparison of secretory signal peptides for heterologous protein expression in microalgae: Expanding the secretion portfolio for Chlamydomonas reinhardtii. PLoS One, 13(2), e0192433. (Year: 2018).*

Dahlin, L. R. (2019). Screening, down-selection, characterization, and genetic tool development in high-productivity microalgae. Colorado School of Mines. (Year: 2019).*

Doyle, S. "UniProt." UniProt, 2018, www.uniprot.org/uniprotkb/A0A378ZXB9/entry. Accessed Jul. 18, 2024. (Year: 2018).*

Dahlin et al., "Development of the high-productivity marine microalga, Picochlorum renovo, as a photosynthetic protein secretion platform", Algal Research, 2021, vol. 54, 102197, pp. 1-7.

* cited by examiner

*Primary Examiner* — Louise W Humphrey
*Assistant Examiner* — Kimberly Breen
(74) *Attorney, Agent, or Firm* — Sam J. Barkley

(57) ABSTRACT

Disclosed herein are methods and compositions for implementing a photosynthetic protein secretion platform.

2 Claims, 5 Drawing Sheets

Specification includes a Sequence Listing.

SEQUENCE LISTING

<160> NUMBER OF SEQ ID NOS: 10

<210> SEQ ID NO 1
<211> LENGTH: 54
<212> TYPE: DNA
<213> ORGANISM: Picochlorum renovo

<400> SEQUENCE: 1
atgatgcttt cctttttac gacgctgttg ctgacagcaa tgttggcatt tggg                54

<210> SEQ ID NO 2
<211> LENGTH: 18
<212> TYPE: PRT
<213> ORGANISM: Picochlorum renovo

<400> SEQUENCE: 2

Met Met Leu Ser Phe Phe Thr Thr Leu Leu Thr Ala Met Leu Ala
1               5                   10                  15

Phe Gly

<210> SEQ ID NO 3
<211> LENGTH: 614
<212> TYPE: PRT
<213> ORGANISM: Picochlorum renovo

<400> SEQUENCE: 3

Met Met Leu Ser Phe Phe Thr Thr Leu Leu Thr Ala Met Leu Ala
1               5                   10                  15

Phe Gly Gln Pro Gly Thr Asp Glu Tyr Lys Tyr Ala Ala Glu Lys Phe
            20                  25                  30

Gln Leu Gly Leu Pro Met Thr Gln Ala Gln Val Ser Ser Ala Asp Asp
        35                  40                  45

Tyr Asp Val Tyr Leu Gln Glu Tyr Lys Glu Ser Asn Pro Ala Leu
    50                  55                  60

Gln Pro Lys Pro Gly Arg Pro Val Glu Glu Phe Tyr Thr Asp Glu Phe
65                  70                  75                  80

Val Lys Ser Glu Trp Lys Lys Phe Ile Lys Met Leu Ile Asn Arg Lys
                85                  90                  95

Asn Val Phe Thr Gly Val His Tyr Tyr Asp Asp Pro Thr Ile Phe Ala
            100                 105                 110

Phe Glu Leu Ala Asn Glu Pro Arg Ala Gln Gly Tyr Asp Ala Lys Ile
        115                 120                 125

Gly Lys Lys Pro Gly Glu Thr Ile Cys Ser Trp Ala Ala Glu Met Thr
    130                 135                 140

Ala Tyr Ile Arg Ser Leu Asp Lys Asn His Met Ile Ser Ile Gly Asp
145                 150                 155                 160

Glu Gly Met Arg Thr Asp Gly Pro Thr Lys Glu Pro His Ser Trp Ile
                165                 170                 175

Asn Thr Gly Tyr Glu Gly Val Asp Phe Val Cys Asn Leu Lys Tyr Ala
            180                 185                 190

Asp Phe Ala Thr Ile His Ser Tyr Pro Asp Ala Trp Gly Met Ser Ala
        195                 200                 205

Asp Gly Gly Tyr Thr Trp Leu Gly Glu Asn Tyr Tyr Lys Asp Arg Arg
    210                 215                 220

Asp Ile Ala His Ser Met Asp Lys Pro Ile Ile Leu Glu Lys Arg Tyr
225                 230                 235                 240

```
Ala Cys Thr Leu Val Trp Ala Val Ser His Tyr Pro Thr Pro Tyr
            245                 250                 255

Gln Tyr Thr Tyr Tyr Gly Tyr Asn Asp Gly Gln Gly Tyr Val Phe Gly
            260                 265                 270

Tyr Thr Gly Pro Asp Thr Asp Gly Lys Ala Ser Val Val Lys Gln Tyr
            275                 280                 285

Glu Tyr Met Asn Ala Leu Asp Glu Ser Arg Val Pro Pro Lys Glu Ile
            290                 295                 300

Ile Glu Pro Pro Thr Asn Gln Cys Ser Asp Val Pro Pro Ser Lys Gln
305                 310                 315                 320

Tyr Thr Cys Gln Gln Gln Lys Asn Trp Gly Lys Cys Asn Glu Pro Trp
                325                 330                 335

Met Lys Gly Tyr Cys Gln Ala Thr Cys Gly Lys Cys Ser Leu Pro Lys
                340                 345                 350

Ser Pro Pro Pro Lys Pro Gly Asn Ser Pro Pro Thr Lys Pro Cys Thr
                355                 360                 365

Asp Val Pro Pro Ser Lys Gln Asp Ser Thr Gly Thr Met Arg Val Gly
            370                 375                 380

Gln Gln Thr Pro Thr Arg Met Ile Thr Arg Ser Ile Ala Arg Arg Leu
385                 390                 395                 400

Thr Thr Gly Gln Pro Ala Lys Ala Ala Val Ser Pro Thr Pro Ser Pro
                405                 410                 415

Pro Gly Val Pro Asp His Thr Asp Val Pro Ser Ser Pro Ala Lys Thr
                420                 425                 430

Arg Pro Pro Arg Thr Thr Arg Ser Asn Lys Arg Gly Arg Asp Gln Cys
                435                 440                 445

Ser Thr Gln Val Ala His Thr Arg Val Glu Glu Val Pro Tyr Thr
            450                 455                 460

Arg Val Glu Glu Glu Gly Ala His Thr Arg Val Glu Glu Gln Val Val
465                 470                 475                 480

Tyr Ala Met Val Glu Leu Thr Pro Pro Thr Ala Arg Lys Arg Gln Arg
                485                 490                 495

Val Arg Arg Thr Lys Tyr Asp Val Arg Asp Glu Glu Asp Thr Arg Val
                500                 505                 510

Ala Leu Arg Leu Cys Gln Thr Lys Lys Glu Ile Gly Val Gly Glu Ala
                515                 520                 525

Ala Thr Ile Leu Gln Ser Leu Lys His Asp Thr Thr Leu Val Val Met
                530                 535                 540

Gln Ala Pro Lys Gln Glu Pro Lys Lys Gly Ala Lys Lys Arg Ser Thr
545                 550                 555                 560

Lys Arg Ser Thr Lys Gly Ser Lys Lys Gly Ala Lys Lys Val Thr Thr
                565                 570                 575

Arg Ala Ser Ser Ser Leu Ser Tyr Pro Ala Gln Ala Asp Phe Ser Met
                580                 585                 590

Leu His Ala Leu Ala Glu Glu Ala Tyr Met Phe Glu Asn Asp Thr Ala
            595                 600                 605

Pro Asp Ala Thr Arg Arg
    610
```

<210> SEQ ID NO 4
<211> LENGTH: 72
<212> TYPE: DNA
<213> ORGANISM: Picochlorum renovo

<400> SEQUENCE: 4
atgaaggctg ccatgagcag agcagggatc ttccttgcag ttgtctttgc cgttgttagt    60
ggagctcacg cg    72

<210> SEQ ID NO 5
<211> LENGTH: 24
<212> TYPE: PRT
<213> ORGANISM: Picochlorum renovo

<400> SEQUENCE: 5

Met Lys Ala Ala Met Ser Arg Ala Gly Ile Phe Leu Ala Val Val Phe
1               5                   10                  15

Ala Val Val Ser Gly Ala His Ala
            20

<210> SEQ ID NO 6
<211> LENGTH: 656
<212> TYPE: PRT
<213> ORGANISM: Picochlorum renovo

<400> SEQUENCE: 6

Met Lys Ala Ala Met Ser Arg Ala Gly Ile Phe Leu Ala Val Val Phe
1               5                   10                  15

Ala Val Val Ser Gly Ala His Ala Thr Asn Cys Ser Ser Ala Asp
            20                  25                  30

Gly Arg Gln Ile Tyr Lys Asp Gly Phe Gln Asp Thr Trp Leu Ser Gly
        35                  40                  45

Ser Gln Gly Thr Val Leu Asp Asp Val Ser Asn Val Thr Ile Arg Pro
    50                  55                  60

Gly Thr Asn Met Ser Leu Ala Ala Glu Ile Gly Ala Phe Ser Thr Phe
65                  70                  75                  80

Ser Met Val Thr Val Val Pro Phe Ser Thr Asn Ser Leu Leu Asp Met
                85                  90                  95

Trp Ile Gln Gly Thr Val Gln Asp Ala Met Leu Tyr Phe Glu Ser
            100                 105                 110

Ser Glu Ser Gln Val Arg Ser Asp Ser Ile Asp Leu Ser Ala Ile Ser
        115                 120                 125

Pro Glu Ser Ile Ala Ala Asp Val Leu Gln Asp Ala Val Arg Ile
    130                 135                 140

Val Gly Pro Asp Ala Ala Asp Trp Phe Arg Leu Ser Val Asn Thr Lys
145                 150                 155                 160

Ile Leu Ala Pro Ser Asn Ala Thr Glu Thr Trp Asp Ser Ile Val Phe
                165                 170                 175

Arg Asp Ala Ser Gly Thr Gly Phe Ser Ile Phe Val Ser Glu Ala Gln
            180                 185                 190

Ile Leu Pro Asn Leu Pro Pro Cys Glu Ser Arg Ala Ser Ser Gly Cys
        195                 200                 205

Ile Gly Asn Val Cys Asn Pro Val Ile Asp Glu Leu Phe Pro Gln Ser
    210                 215                 220

Asp Ala Val Pro Leu Phe Gly Tyr Gly Pro Ile Ala Gln Glu Ile Ser
225                 230                 235                 240

Asp Glu Ile Ser Ala Ala Gly Val Arg Gly Ile Ser Leu Ile Ala Lys
                245                 250                 255

Leu Phe Lys Asn Ile Thr Tyr Ala Glu Val Phe Glu Met Cys Ala Lys
            260                 265                 270

Leu Gln Gly Gln Glu Gln Gly Ser Gly Pro Glu Asp Val Phe Val Thr
                275                 280                 285

Ser Val Glu Ile Leu Glu Ala Arg Ser Thr Ile Ser Pro Asn Val Ile
290                 295                 300

Ala Val Cys Glu Ile Asp Ala Thr Thr Thr Ser Leu Ala Gln Ala Asp
305                 310                 315                 320

Ile Met Ala Pro Val Glu Trp Pro Leu Leu Thr Val Arg Ser Tyr Ser
                325                 330                 335

Phe Glu Asn Ile Thr Thr Met Arg Ala Met Val Thr Thr Lys Val Ser
                340                 345                 350

Tyr Phe Asp Arg Asp Gly Ile Ala Thr Thr Asn Ser Asp Asp Leu Leu
                355                 360                 365

Ala Ser Thr Asp Ala Ala Cys Pro Gly Ile Pro Trp Gly Leu Ser Arg
370                 375                 380

Leu Asp Gln Pro Asn Leu Pro Leu Asp Asn Val Phe Lys Pro Gly Leu
385                 390                 395                 400

Thr Gly Ser Gly Val His Ile Tyr Val Leu Asp Thr Gly Val Ser Ser
                405                 410                 415

His Ser Asp Phe Thr Gly Arg Ile Gly Ala Gly Val Ser Cys Phe Thr
                420                 425                 430

Gly Thr Cys Thr Ser Gly Asn Phe Ala Asp Ala Asn Gly His Gly Thr
                435                 440                 445

His Val Ala Gly Thr Ala Ala Gly Thr Cys Phe Gly Val Ala Lys Lys
                450                 455                 460

Ala Ile His Pro Val Lys Val Leu Ser Asp Ser Gly Ser Gly Ser
465                 470                 475                 480

Tyr Ser Gly Ile Ile Asn Gly Ile Lys Phe Ser Val Gln Asn Ser Lys
                485                 490                 495

Asn Asn Gly Trp Arg Gly Val Ile Asn Met Ser Leu Gly Gly Gly Ser
                500                 505                 510

Ser Ala Ser Leu Asn Ser Ala Val Asn Glu Ala Val Ser Lys Gly Leu
                515                 520                 525

Val Val Ala Ala Ala Gly Asn Asp Tyr Ala Ala Asn Ala Cys Thr
530                 535                 540

Lys Ser Pro Ala Ser Ala Asn Ala Leu Thr Val Ala Ser Val Thr
545                 550                 555                 560

Lys Gln Asp Thr Ala Ser Ser Phe Ser Asn Val Gly Ser Cys Val Asp
                565                 570                 575

Ile Trp Ala Pro Gly Thr Arg Val Ala Ser Ala Ser Asn Thr Asn Phe
                580                 585                 590

Asn Gly Tyr Lys Thr Leu Ser Gly Thr Ser Met Ala Thr Pro His Val
                595                 600                 605

Ala Gly Ala Ala Ala Leu Tyr Leu Gln Lys Tyr Pro Ser Ala Ser Pro
610                 615                 620

Gly Gln Val Arg Gln Gly Leu Leu Lys Ala Ser Val Gln Arg Asn Leu
625                 630                 635                 640

Tyr Pro Gln Thr Thr Thr Ser Leu Leu Gln Ala Tyr Ser Ala Val Phe
                645                 650                 655

<210> SEQ ID NO 7
<211> LENGTH: 21
<212> TYPE: PRT
<213> ORGANISM: Artificial sequence
<220> FEATURE:
<223> OTHER INFORMATION: expressed portion of pLRD40

```
<400> SEQUENCE: 7

Pro Met Asn Lys Phe Ala Leu Cys Val Leu Ala Phe Ala Ala Thr Ala
1               5                   10                  15

Val Ser Val Ser Gly
            20

<210> SEQ ID NO 8
<211> LENGTH: 25
<212> TYPE: PRT
<213> ORGANISM: Artificial sequence
<220> FEATURE:
<223> OTHER INFORMATION: expressed portion of pLRD41

<400> SEQUENCE: 8

Pro Met Lys Gly Asn Leu Ala Arg His Ser Leu Phe Ala Leu Phe Val
1               5                   10                  15

Ala Val Phe Leu Ser Ala Ala Gln Ser
            20                  25

<210> SEQ ID NO 9
<211> LENGTH: 30
<212> TYPE: PRT
<213> ORGANISM: Artificial sequence
<220> FEATURE:
<223> OTHER INFORMATION: expressed portion of pLRD42

<400> SEQUENCE: 9

Pro Met Gly Phe Ser Thr Asn Asn Lys Ser Arg Ile Val Ala Leu
1               5                   10                  15

Phe Ala Leu Leu Phe Ile Ser Ala Ala Thr Thr Cys Ser Ala
            20                  25                  30

<210> SEQ ID NO 10
<211> LENGTH: 25
<212> TYPE: PRT
<213> ORGANISM: Artificial sequence
<220> FEATURE:
<223> OTHER INFORMATION: expressed portion of pLRD43

<400> SEQUENCE: 10

Pro Met Met Met Arg Gly Ser Thr Phe Ala Ser Leu Gly Leu Pro Leu
1               5                   10                  15

Leu Ala Val Cys Ile Gln Gly Asn Ala
            20                  25
```

PHOTOSYNTHETIC PROTEIN SECRETION PLATFORM

CROSS-REFERENCE TO RELATED APPLICATIONS

This application claims priority under 35 U.S.C. § 119 to U.S. provisional patent application No. 63/146,469 filed on 5 Feb. 2021, the contents of which are hereby incorporated in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via EFS-web and is hereby incorporated by reference in its entirety. The ASCII copy as filed herewith was originally created on 1 May 2024. The ASCII copy as filed herewith is named NREL 21-22_ST25.txt, is 13,496 bytes in size and is submitted with the instant application.

BACKGROUND

Microalgae are remarkable in their ability to convert $CO_2$ and sunlight into renewable biomass and bioproducts. Here, we have established a novel photosynthetic protein production platform via computational prediction and genetic engineering using native microalgal protein secretory signal peptides to achieve functional secretion of the fluorescent protein mCherry. Importantly, this work was conducted in the recently characterized alga *Picochlorum renovo*, an alga of industrial interest due to its rapid growth rate, tolerance to both high temperature and salinity, and genetically tractable nuclear and chloroplast genomes. Genomic queries allowed the identification of native secretory signal peptides, which were N-terminally fused to mCherry allowing for secretion into the culture supernatant. Further characterization revealed no impact on fitness, a production rate of 0.19 mg/L/day, and titer of 0.37 mg/L of transgenic mCherry protein in culture supernatant. These findings lay the foundation for applied genetic engineering approaches that could enable $CO_2$-sequestering, sustainable photoproduction of industrially relevant enzymes at low cost.

SUMMARY

Exemplary embodiments of the invention disclosed herein provide an overview of construct design utilized for testing secretion signals. Resistance to bleomycin family antibiotics is conferred by the ble gene. Bolded and underlined P represents the proline resultant from 2A ribosomal skipping. Red text in alignment represents hydrophobic amino acids, asterisk denotes conserved amino acid.

In an aspect, disclosed herein is a novel photosynthetic protein secretion platform comprising a non-naturally occurring *Picochlorum renovo*. In an embodiment, the novel photosynthetic protein secretion platform comprises a non-naturally occurring *Picochlorum renovo* that comprises the secretion of the fluorescent protein mCherry. In an embodiment, the novel photosynthetic protein secretion platform comprises a non-naturally occurring *Picochlorum renovo* that comprises a secretory signal peptide. In an embodiment, the novel photosynthetic protein secretion platform comprises a non-naturally occurring *Picochlorum renovo* that comprises a secretory signal peptide having the DNA sequence of SEQ ID NO: 1. In an embodiment, the novel photosynthetic protein secretion platform comprises a secretory signal peptide having the amino acid sequence of SEQ ID NO: 2. In an embodiment, the novel photosynthetic protein secretion platform of claim 2 comprising the expression of protein 5515 (SEQ ID NO: 3). In an embodiment, the novel photosynthetic protein secretion platform comprises a non-naturally occurring *Picochlorum renovo* that comprises a secretory signal peptide having the DNA sequence of SEQ ID NO: 4. In an embodiment, the novel photosynthetic protein secretion platform comprises a non-naturally occurring *Picochlorum renovo* that comprises a secretory signal peptide having the amino acid sequence of SEQ ID NO: 5. In an embodiment, the novel photosynthetic protein secretion platform comprises the expression of protein 1410 SP (SEQ ID NO: 6).

In an aspect, disclosed herein is a method for a photosynthetic protein secretion platform comprising the step of using a non-naturally occurring *Picochlorum renovo* for the expression of a protein of interest. In an embodiment, the photosynthetic protein secretion platform comprises the secretion of the fluorescent protein mCherry. In an embodiment, the photosynthetic protein secretion platform comprises a secretory signal peptide. In an embodiment, the photosynthetic protein secretion platform comprises the DNA sequence of SEQ ID NO: 1. In an embodiment, the photosynthetic protein secretion platform comprises the amino acid sequence of SEQ ID NO: 2. In an embodiment, the photosynthetic protein secretion platform comprises the expression of protein 5515 (SEQ ID NO: 3). In an embodiment, the photosynthetic protein secretion platform comprises a secretory signal peptide having the DNA sequence of SEQ ID NO: 4. In an embodiment, the photosynthetic protein secretion platform comprises a secretory signal peptide having the amino acid sequence of SEQ ID NO: 5. In an embodiment, the photosynthetic protein secretion platform comprises the expression of protein 1410 SP (SEQ ID NO: 6).

Other objects, advantages, and novel features of the present invention will become apparent from the following detailed description of the invention when considered in conjunction with the accompanying drawings.

DETAILED DESCRIPTION

Figure 1:
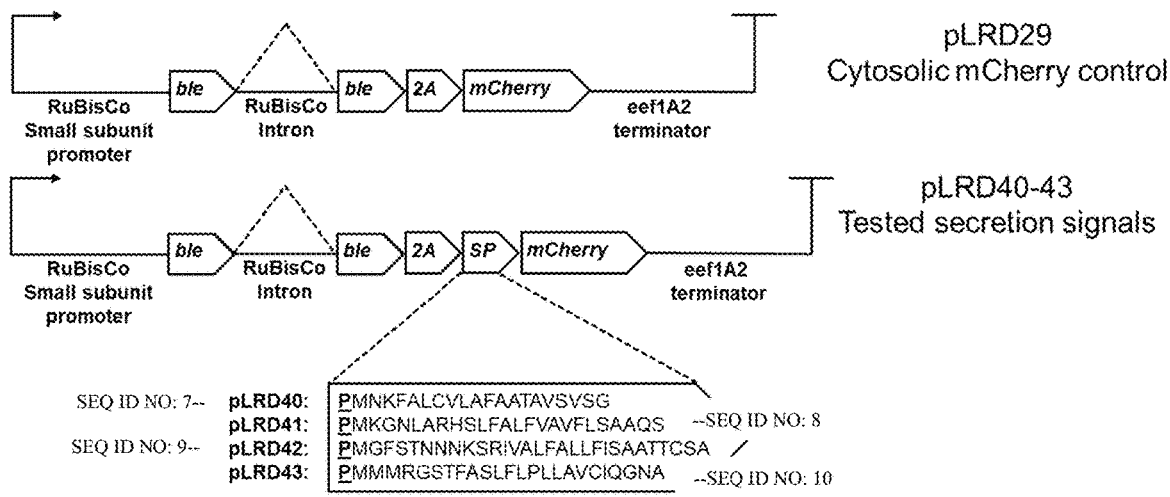
FIG. 1 depicts an overview of construct design utilized for testing secretion signals. Resistance to bleomycin family antibiotics is conferred by the ble gene. SEQ ID NO: 7 is PMNKFALCVLAFAATAVSVSG which is the sequence of tested secretion signal pLRD40; SEQ ID NO: 8 is PMKGNLARHSLFALFVAVFLSAAQS which is the sequence of tested secretion signal pLRD41; SEQ ID NO: 9 is PMGFSTNNNKSRIVALFALLFISAATTCSA which is the sequence of tested secretion signal pLRD42; SEQ ID NO: 10 is PMMMRGSTFASLGLPLLAVCIQGNA which is the sequence of tested secretion signal pLRD43. Bolded and underlined P represents the proline resultant from 2A ribosomal skipping. Hydrophobic amino acid residues in the Clustal Omega Alignment portion of FIG. 1 are represented here as underlined and bold: 43 MMMRGS-----T---FASLFLPLLAVCIQGNA; 42 MGFSTNNNKSRIVALFALLFISAATTCSA---; 40---------MNKFALCVLA- FAATAVSVSG---; and
41-MKGNLARHSLFALFVAVFLSAAQS------

Disclosed herein are microalgae are a promising source of renewable biomass, and photobiocatalysts that can be utilized for the production of a myriad of products. In particular, phototrophic protein production has the potential to significantly lower the cost of commodity enzymes, as such systems are not reliant on reduced carbon (e.g glucose) for growth, which can account for 12-57% of the cost to produce commodity enzymes heterotrophically. Additionally, unlike heterotrophic systems, such phototrophic production systems have the potential to remove $CO_2$ from the atmosphere, ameliorating problems associated with climate change. Microalgae offer further advantages over higher plants, due to their relatively rapid growth rate, for example achieving 5.4 to 10 fold greater areal productivity when compared to corn grain, and mass cultivation capacity in saline waters on non-arable land.

High photosynthetic protein production yields can be obtained in both algae and terrestrial plants, with yields as high as 74% of total protein via chloroplast engineering. However, such plastidial expression approaches lead to intracellular accumulation of transgenic proteins, resulting in cost and sustainability hurdles associated with protein recovery and purification. Unlike terrestrial crops, the aquatic nature of microalgae presents the unique potential for direct protein secretion and purification from culture supernatant. This simplified purification process has recently been demonstrated in the model alga, *Chlamydomonas reinhardtii*, wherein a hydrophobic protein tag was included in the protein of interest, allowing for a scalable, aqueous two-phase protein extraction system. Targeting of proteins to explicit intracellular or extracellular locations is frequently accomplished via inclusion of N-terminal localization peptides. One application of these has been targeting of proteins to the chloroplast, which has been established for a variety of algae including *Chlamydomonas, Phaeodactylum, Nannochloropsis, Dunaliella*, and *Chlorella*. However, to date, transgenic protein secretion into culture supernatant via N-terminal localization peptides has only been established in the model algae *C. reinhardtii* and *Phaeodactylum tricornutum*.

Signal peptides (SP) have the capacity to direct proteins to anywhere in the secretory pathway, such as the endoplasmic reticulum, Golgi apparatus, insertion into cellular membranes or secretion from the cell. These peptides are relatively short N-terminal sequences (typically 16-30 amino acids) that work in conjunction with retention motifs for proper protein localization. In *Chlamydomonas* a number of biotechnologically relevant proteins have been successfully secreted by these means, such as xylanase, ice binding protein, human growth factor, human vascular endothelial growth factor, and human erythropoietin. Fluorescent proteins and luciferase have proved useful for optimization of various aspects of secretion, as detection and relative quantification can be rapidly assessed. For example, the use of tandem serine-proline repeats to increase the secreted yield of the fluorescent protein Venus.

In recent years, a number of *Picochlorum* isolates have been characterized and recognized for several unique characteristics important for biotechnological applications. In general, algae of the genus *Picochlorum* are capable of growth in hyper-saline waters, relatively high temperatures (~35° C. optimal), resilient to high light intensities, and display a rapid growth rate (~2 hr doubling time) and high areal productivity (>34 g/m$^2$/day). Importantly, these algae are genetically tractable, with both the nuclear and chloroplast genomes transformed to date; notably CRISPR Cas9 ribonuclear protein complexes have recently been utilized for knockout of nuclear encoded genes, In the work presented here, we sought to expand the genetic capabilities in this genus via the establishment of N-terminal secretory signal peptides allowing functional transgenic protein to accumulate in culture media. This was accomplished via genomics-guided identification of native secretory signal peptides in the proteome of *P. renovo*. These signal peptides were incorporated into our previously established genetic engineering construct, allowing for secretion of the fluorescent protein mCherry. Fluorometric analysis indicated ~24% of the mCherry was secreted from the cell, at a titer of 0.37 mg/L and production rate of 0.19 mg/L/day. This work expands the capabilities of this emerging model algal system and lays the foundation for the development of a low cost, industrially relevant photosynthetic protein production platform, and could be leveraged for the secretion of proteins that may aid in microalgal cultivation.

Results and Discussion

Identification of Native *P. renovo* Secretory Signal Peptides

Building on our previous work which established intracellular mCherry expression in *P. renovo* (30), we sought to establish a platform for extracellular secretion via incorporation of native secretory signal peptides on the N-terminus of mCherry. To determine appropriate secretory signal peptides, a number of publicly available prediction algorithms were utilized (Table 1). First, SignalP (5.0) was used to down-select sequences from the proteome that contained a high probability signal peptide and predicted peptide length. The conserved domain database was then utilized to identify domains in the native proteins, to lend insight into potential extracellular functionality. Finally, DeepLoc (1.0) was used to provide additional predictive evidence for extracellular proteins. Ultimately 4 native proteins were identified that we hypothesized had a high likelihood of being extracellularly secreted, with high probability in the predicted signal peptide length. These proteins were putatively annotated as proteins of unknown function, in the genomic annotations for *P. renovo*. When queried against the conserved domain database, these proteins contained predicted Fasciclin or Fibronectin type III domains (Table 1), which have been demonstrated to function in the extracellular space for cell adhesion and extracellular matrix formation. Multiple sequence alignment of the signal peptides via Clustal Omega showed little homology between the sequences, which is a common observation of different secretory signal peptides. However, a canonical stretch of ~10 hydrophobic amino acids was observed in all sequences (FIG. 1). Thus, we concluded that these native proteins were likely to be secreted proteins and proceeded to test the predicted signal peptides for secretion of transgenic mCherry, as depicted in FIG. 1.

TABLE 1

Characterization of native proteins and their associated localization

|  | Native protein (002469) pLRD40 | Native protein (005295) pLRD41 | Native protein (008562) pLRD42 | Native protein (008366) pLRD43 |
| --- | --- | --- | --- | --- |
| Putative Annotation | Protein of unknown function | Protein of unknown function | Uncharacterized protein sll1483 (Synechocystis PCC 6803) | Protein of unknown function |
| Conserved Domain Database | Fasciclin | Fibronectin type III | Fasciclin | Fibronectin type III |
| SignalP-5.0 Predictions: | | | | |
| Localization (Likelihood) | Signal Peptide (0.9962) | Signal Peptide (0.9994) | Signal Peptide (0.966) | Signal Peptide (0.9981) |
| Peptide Length (Probability) | 20 (0.7810) | 24 (0.8904) | 29 (0.8305) | 24 (0.8724) |
| DeepLoc-1.0 Predictions: | | | | |
| Extracellular | 0.8308 | 0.998 | 0.2718 | 0.6227 |
| Cytoplasm | 0.0553 | 0.0005 | 0.0311 | 0.2103 |
| Mitochondrion | 0.0585 | 0 | 0.2464 | 0.0733 |
| Lysosome | 0.0232 | 0.001 | 0.0247 | 0.0249 |
| Cell membrane | 0.0084 | 0.0001 | 0.0151 | 0.0233 |
| Plastid | 0.0083 | 0 | 0.387 | 0.0193 |
| Peroxisome | 0.0008 | 0 | 0.005 | 0.0118 |
| Endoplasmic reticulum | 0.0147 | 0.0004 | 0.0182 | 0.0086 |
| Nucleus | 0 | 0 | 0.0005 | 0.0032 |
| Golgi apparatus | 0 | 0 | 0.0002 | 0.0025 |

Transgenic Secretory Signal Peptide Testing

Figure 2:
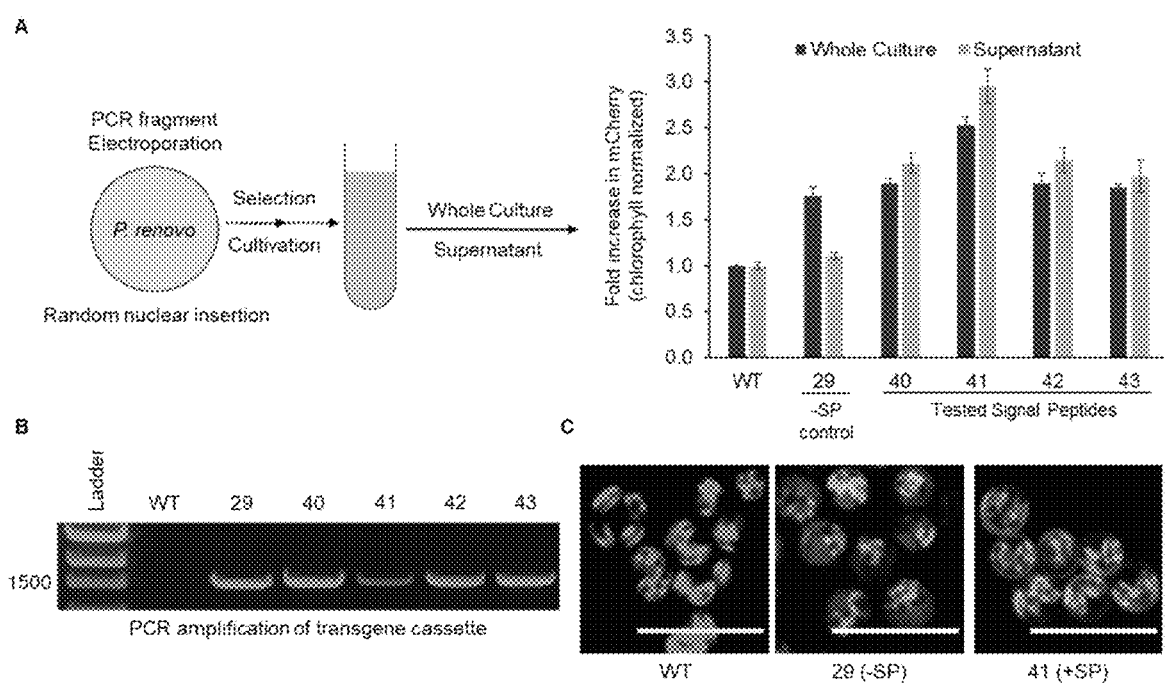
FIG. 2 depicts (A) an overview of the assay used to determine mCherry fluorescence in culture and supernatant. WT is a wild type culture, 29 is an mCherry expressing non-secreting control, 40-43 are tested secretion signals. Values presented represent an average of n=3 biological replicates from a single clonal isolate, error bars represent the standard deviation of these replicates. (B) a PCR analysis of transgenic clones (C) Confocal microscopy of wild type, non-secreting, and a secreting cell line from construct 41, 10 μm scale bar

In the model alga *Chlamydomonas reinhardtii* it has been previously demonstrated that successful secretion can be achieved when the signal peptide is integrated into an expression cassette upstream of a gene of interest. As such, we paralleled this approach in *P. renovo*, utilizing phleomycin as the selectable marker (conferred by the ble gene), followed by the 2A peptide which was utilized to link the selection marker and downstream mCherry gene; the 2A peptide causes ribosomal skipping, and thus leads to the translation of two separate proteins. Transgenic colonies were readily obtained when the signal peptide was included as an N-terminal fusion to mCherry (pLRD40-43, FIG. 1). Successful transgene integration was confirmed via colony PCR (FIG. 2B). A fluorescent plate reader assay was utilized to determine both intracellular and extracellular mCherry as depicted in FIG. 2A, with wild type and a non-secreting, intracellular mCherry clone serving as negative controls. When analyzing the whole culture (cells and supernatant), a 1.7 to 2.5-fold increase in mCherry fluorescence was observed as compared to the wild type control, for both intracellular and putative extracellular mCherry secreting clones. To assay supernatant, cells were pelleted, and the supernatant was analyzed for mCherry fluorescence. Intracellular mCherry expressing P. renovo (pLRD29) supernatant displayed comparable fluorescence measurements to the WT control (1.1 vs 1.0). Conversely, constructs containing a putative secretory signal peptide displayed 2-3-fold higher mCherry fluorescence in the supernatant (FIG. 2A). Interestingly, the fluorescence results for the clonal isolate analyzed for pLRD41 was notably higher than for the other constructs; this could be due to positional effects or multiple insertions of the transgene cassette, as we have previously noted similar variations in expression for intracellular mCherry.

Figure 3:
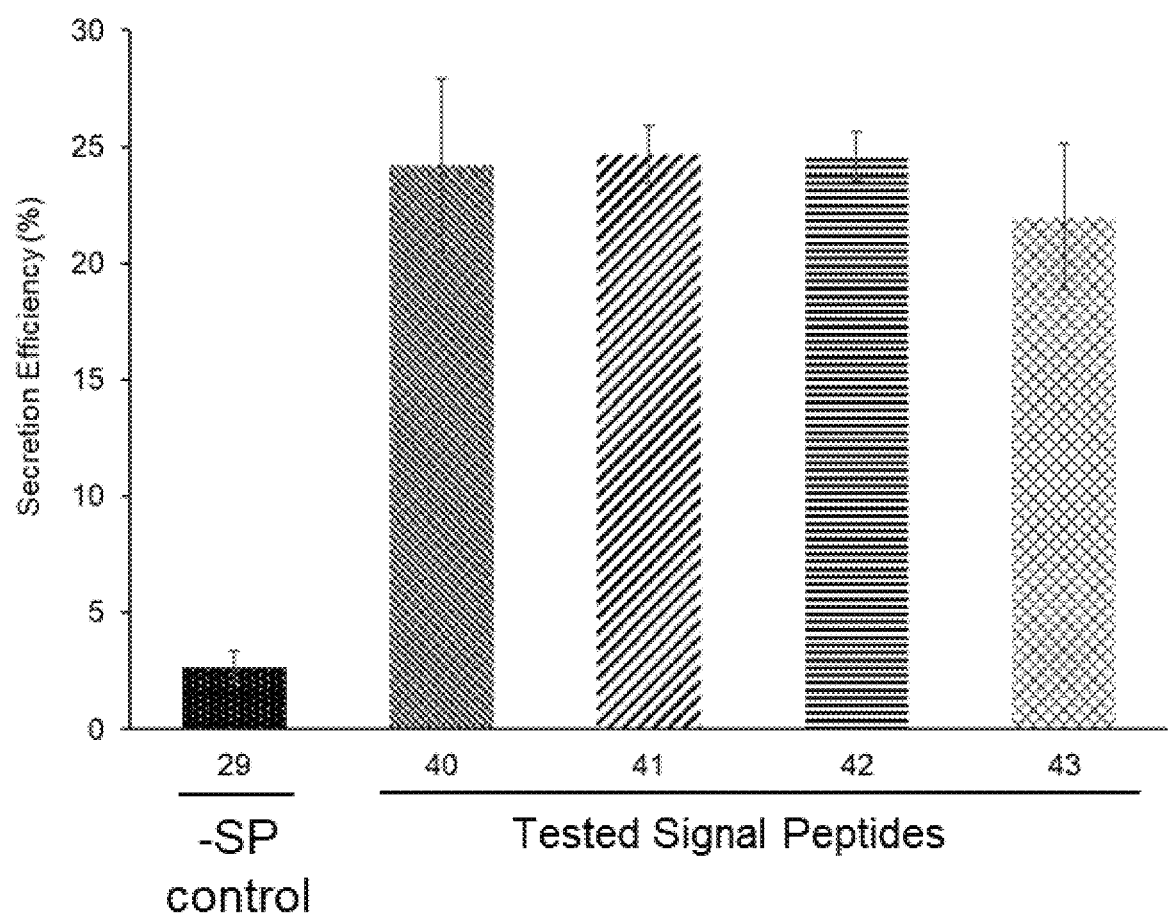
FIG. 3 depicts secretion efficiency as a percentage of supernatant fluorescence compared to the whole culture with background (WT) signal subtracted. Values presented represent an average of n=3 biological replicates from a single clonal isolate, error bars represent the standard deviation of these replicates.

Confocal microscopy showed a distinct differential between the intracellular mCherry accumulating isolate (pLRD29) and a secreting isolate (pLRD41). Intracellular mCherry accumulated throughout the cell (excluding the chloroplast), while the secreting isolate showed mCherry localized to the cell periphery (FIG. 2C). This localization could be due to retention in the periplasm, or adsorption to the cell wall. Future studies will further evaluate the nature of retained transgenic protein. To determine the efficiency of secretion, as compared to intracellular levels, background levels of fluorescent noise (normalized to chlorophyll fluorescence) from the wildtype were subtracted from mCherry expressing clones, yielding a proxy for mCherry quantity in the whole culture (cells and supernatant) and supernatant. Dividing the supernatant value by the whole culture yielded a secretion efficiency of 22-25% for the 4 secretory signal peptides tested. When treated similarly, the non-secreting mCherry control yielded a secretion efficiency of 3%, likely reflective of error in the measurement and mCherry released from the cell during division or lysis (FIG. 3). These results suggest that approximately 75% of the mCherry produced is not secreted from the cell; significant improvements can likely be obtained through a variety of methods, discussed below.

Figure 4:
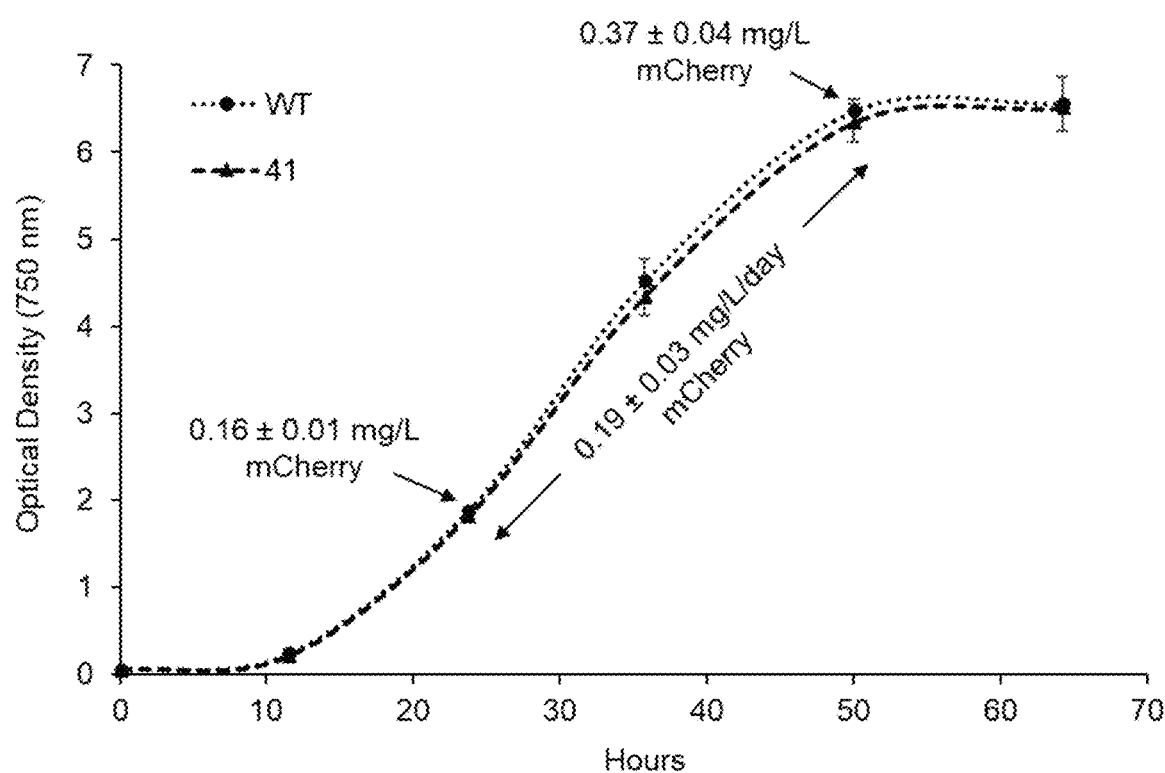
FIG. 4 depicts growth comparison of WT and the highest mCherry secreting clone, pLRD41. Values presented represent an average and standard deviation of n=4 biological replicates. Secreted mCherry concentration in supernatant, and associated production rate is noted.
Figure 5:
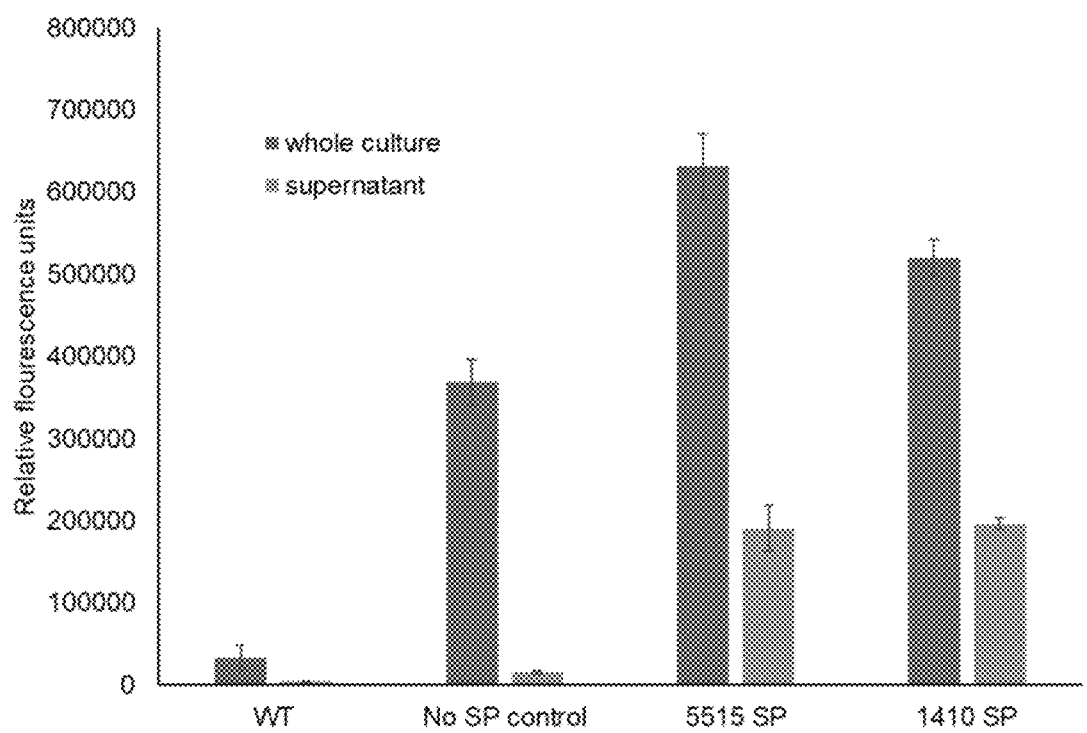
FIG. 5 depicts the relative fluorescence units of two signal peptides (SEQ ID NO. 1 for DNA sequence ATGATGCTTTCCTTTTT-TACGACGCTGTTGCTGACAGCAATGTTGGCAT-TTGGGof signal peptide with SEQ ID NO. 2 for amino acid sequence of MMLSFFTTLLLLTAMLAFG) for protein 5515 (SEQ ID NO: 3 MMLSFFTTLLLLTAMLAFGQPGT-DEYKYAAEKFQLGLPMTQAQVSSADDYDVYLQEYK KESNPALQPKPGRPVEEFYTDEFVKSEWKKFIKM-LINRKNVFTGVHYYDDPTIFAFELAN EPRAQGYDAKIGKKPGETICSWAAEMTAY-IRSLDKNHMISIGDEGMRTDGPTKEPHSWI NTGYEGVDFVCNLKYADFATIHSYPDAWGM-SADGGYTWLGENYYKDRRDIAHSMDK PIILEKRY-ACTLVWAVSHYPTTPYQYTYYGY-NDGQGYVFGYTGPDTDGKASVVKQYEY MNALDESRVPPKEIIEPPTNQCSDVPPSKQYTCQQQ-KNWGKCNEPWMKGYCQATCGKC SLPK-SPPPKPGNSPPTKPCTDVPPSKQDSTGTMRVGQQTP-TRMITRSIARRLTTGQPAKA AVSPTPSPPGVPDHTDVPSSPAKTRPPRTTRSNKR-GRDQCSTQVAHTRVEEEVPYTRVEE EGAHTRVE-EQVVYAMVELTPPTARKRQRVRRTKYDVRDEEDTR-VALRLCQTKKEIGVG EAATILQSLKHDTTLVVMQAPKQEPKK-GAKKRSTKRSTKGSKKGAKKVTTRASSSLSYP AQADFSMLHALAEEAYMFENDTAPDATRR) and SEQ ID NO. 4 for DNA sequence ATGAAGGCTGCCAT-GAGCAGAGCAGG-GATCTTCCTTGCAGTTGTCTTTGCCGTTGTT AGTG-GAGCTCACGCG for amino acid sequence of MKAAMSRAGIFLAVVFAVVSGAHA (SEQ ID NO: 5) for protein 1410 SP (SEQ ID NO 6 MKAAMSRAGIFLA-VVFAVVSGAHAATNCS-SADGRQIYKDGFQDTWLSGSQGTVLDDV SNVTIRPGTNMSLAAEIGAFSTFSMVTVVPFSTNSLL-DMWIQGTVVQDAMLYFESSESQ VRSDSIDLSAISP-ESIAAADVLQDAVRIVGPDAADWFRLSVNT-KILAPSNATETWDSIVFR DASGTGFSIFVSEAQIL-PNLPPCESRASSGCIGNVCNPVIDELFPQS-DAVPLFGYGPIAQEIS DEISAAGVRGISLIAK-LFKNITYAEVFEMCAKLQGQEQGSGPEDVFVTSVEI-LEARSTISP NVIAVCEIDATTTSLAQADI-MAPVEWPLLTVRSYSFENITTM-RAMVTTKVSYFDRDGIAT TNSDDLLASTDAACPGIP-WGLSRLDQPNLPLDNVFKPGLTGSGVHIYVLDTGV-SSHSDFT GRIGAGVSCFTGTCTSGNFADANGHGTH-VAGTAAGTCFGVAKKAIIHPVKVLSDSGSGS YSGI-INGIKFSVQNSKNNGWRGVINMSLGGGSSASLN-SAVNEAVSKGLVVAAAAGNDY AANACTKSPASAANALTVASVTKQD-TASSFSNVGSCVDIWAPGTRVASASNTNFNGYK TLSGTSMATPHVAGAAALYLQKYP-SASPGQVRQGLLKASVQRNLYPQTTTSLLQAYSA VF) in the whole culture and supernatant.

We next characterized growth of the highest mCherry producing clone, pLRD41 (FIG. 2A), to determine any growth alterations due to transgene production and secretion, as severe growth defects could limit biotechnological relevance. As shown in FIG. 4, we did not observe a growth differential between wild type and the secreting clone, based on optical density (750 nm) growth curves. This suggests little-to-no metabolic burden placed on the cells due to transgene protein production, under the conditions tested here (FIG. 4).

We further characterized secreted mCherry titers via a microplate reader assay utilizing a standard curve made from purified mCherry protein. This yielded a max titer of 0.37±0.04 mg/L, and production rate of 0.19±0.03 mg/L/day of transgenic mCherry (FIG. 4). This production rate is similar to that reported for an analogous construct used in Chlamydomonas reinhardtii, and similar titer to that reported in Phaeodactylum tricornutum. However, titers of secreted transgenes have been reported as high as 15.1 mg/L at a productivity of 2.13 mg/L/day when using serine-proline repeats in a cell wall deficient C. reinhardtii strain grown on TAP media. It is notable though that cell wall deficient C. reinhardtii has been demonstrated to secrete unassembled cell wall proteins into culture media, hindering downstream purification processes. Follow on studies will determine the purity of secreted protein from P. renovo in culture supernatant. Further, the system developed herein is a strictly photoautotrophic platform, without the need for additional reduced carbon (e.g. acetate).

To optimize secretion efficiency and secreted protein titer, a number of strategies could be employed, such as the use of varied promoters, serine-proline repeats, or the overexpression of folding chaperons. Identification of a promoter stronger than the native RuBisCo small subunit promoter utilized here could allow for increased protein titer. For example, in Chlamydomonas early work identified that transcription could be enhanced via integration of a heat shock protein promoter upstream of a RuBisCo promoter, in turn greatly increasing protein accumulation. More recent work has identified synthetic promoters in C. reinhardtii, allowing for tunable gene expression, and subsequently tunable protein production. As shown in FIG. 2A, the clone analyzed from pLRD41 had higher levels of both intracellular and extracellular mCherry fluorescence. Thus, we hypothesize that increased protein production via expression enhancements at the transcriptional or translation level has the potential to yield higher secreted protein titers. C-terminally fused glycomodules consisting of serine-proline repeats has been shown to increase both the yield and stability of secreted proteins. This strategy has been demonstrated in Chlamydomonas and a variety of plant cell cultures, and thus offers a promising avenue to increase yield and stability in Picochlorum isolates. Additional strategies employed in other eukaryotic systems to optimize protein secretion also present promising approaches for follow-on studies. For example, the α-MF (mating factor) signal sequence from S. cerevisiae has been utilized for secretion, and directed evolution of this sequence allowed for a 16-fold increase in secretion of a particular protein. Another successful strategy employed in yeast is the overexpression of folding helper proteins. Secreted transgenes may overwhelm the folding capacity of the endoplasmic reticulum, leading to aggregation of unfolded proteins and reduced secretion efficiency. To overcome this researchers have overexpressed binding protein (BiP/kar2), which led to a 20-fold increase in extracellular transgene content. Querying of the Picochlorum renovo genome identified a homolog to BiP/kar2 with 60% amino acid identity, indicating this could be a viable strategy for secretion improvement.

The efficiency of ribosomal skipping of the 2A peptide utilized in this study remains unknown, and represents an additional target for secretion optimization, as if ribosomal skipping does not occur the signal peptide will remain internally located between the selection marker and gene of interest, potentially hindering secretion and gene of interest functionality. Numerous 2A peptides are available from a variety of viruses, and screening of these in other systems has allowed for optimization of ribosomal skipping. Alternatively, these secretory signal peptides could be used to express proteins from a promoter different than that used for selection of transgenic algae, thus bypassing the need for the 2A peptide. We have previously characterized additional promoters functional in *P. renovo* that could be used for this purpose. The successful identification of 4 unique secretory signal peptides will allow for optimized secretion of various transgenes, as the optimal secretory signal peptide varies depending on the protein being secreted. When queried against the genome of another *Picochlorum* species of industrial relevance, *Picochlorum celeri*, the secretion signal peptides described herein shared 93-96% homology (1-2 amino acid alteration) (54). This is suggestive that the work described here will be readily translatable to additional *Picochlorum* isolates.

In conclusion, we have advanced the field of *Picochlorum* biotechnology via the identification of four unique secretory signal peptides from *P. renovo* that lead to secretion of functional protein into culture supernatant. We envision a myriad of potential uses for this technology such as secretion of industrial enzymes (e.g. hydrolases), enzymes enabling enhanced CO2 capture, pest resistance, and therapeutic proteins.

Methods

Secretion Signal Identification

All coding sequences from the annotated *P. renovo* genome were extracted and translated into protein sequences utilizing Geneious Prime software. These protein sequences were then analyzed en masse in the Signal P (5.0) prediction server to identify proteins containing a signal peptide, and determination of the predicted signal peptide length. Proteins with predicted signal peptides were then queried against the Conserved Domain Database to identify domains in the native proteins that are known to function in the extracellular space, as this approach would allow elimination of proteins localized elsewhere in the secretory pathway (e.g. endoplasmic reticulum). DeepLoc (1.0) was utilized for additional computational evidence of protein localization. To determine the extent of homology between identified signal peptides Clustal Omega was utilized to align sequences. Default settings were utilized for all prediction algorithms.

Construct Assembly and Algal Transformation

The predicted secretion peptides were cloned into the previously established pLRD29 plasmid (intracellular mCherry) by utilizing phosphorylated oligos containing tails of the signal peptide (Integrated DNA Technologies), and PCR amplified with pLRD29 as a template. This PCR product was DpnI digested, gel purified, and ligated (T7 DNA ligase, New England BioLabs), followed by transformation into *E. coli* (Stellar cells, Takara) for downstream plasmid preparation and sequence verification.

Transformation of *P. renovo* was carried out as described previously (30). Briefly, a PCR product was generated containing all necessary genetic elements (oligos oLRD 49 and 11), and spin column purified. 3 ug of this DNA was mixed with 10 OD units (~475×106 cells) of sorbitol washed early stage *P. renovo* cells and electroporated using a set time constant and voltage of 2200 volts and 25 ms in an ice cold 2 mm gap cuvette.

After a 15-minute room temperature recovery these cells were plated on selection.

Transgenic colonies appeared after 5 days and were further evaluated for mCherry production. Transgene integration into the algae was confirmed via colony PCR. Cells (~5 µL) were scraped from an agar plate and heated at 95° C. for 25 minutes in 20 µL of Y-PER (ThermoFisher). Following heating samples were diluted with 150 µL of nuclease free water (Ambion). 1 µL of diluted lysate was used for PCR analysis in a 20 µL reaction using Q5 polymerase (New England BioLabs) and visualized via gel electrophoresis in a 1.5% agarose gel with SYBR Safe DNA gel stain (ThermoFisher). Primers utilized were oLRD 73 and 78, as described in Dahlin et al. 2019.

Fluorescence and Growth Assay

To measure mCherry fluorescence (FIGS. 2 and 3), one representative mCherry expressing transformant for each construct tested was grown in glass test tubes with 4 mL of culture media (NM2, 8.75 g/L salinity), and mixed daily via vortexing. Culture conditions were 33° C., 150 µmol m$^{-2}$ s$^{-1}$ (fluorescent lighting), and 1.5% CO2. Mid-log phase cells were analyzed for mCherry and chlorophyll fluorescence utilizing a TECAN M Plex microplate reader. mCherry was analyzed using an excitation wavelength of 572 nm, with a 9 nm bandwidth, and an emission wavelength of 610 nm with a 20 nm bandwidth, gain was set to 220. Chlorophyll autofluorescence was measured with an excitation wavelength of 450 nm, with a 9 nm bandwidth, and an emission wavelength of 680 nm with a 20 nm bandwidth, gain was set to 105. To quantify whole culture measurements, 200 uL of cells and supernatant were loaded into a flat black 96 well plate. To quantify supernatant, 250 uL of culture was centrifuged (12,000 g for 2 mins), 200 uL of the supernatant was transferred to a flat black 96 well plate. Data was normalized to culture chlorophyll autofluorescence to account for differences (targeting <5% variance) in culture density. These cultures and associated data were also utilized for the determination of secretion efficiency.

To compare growth of wild type and an mCherry secreting clone (pLRD41), 50 mL of culture was grown in the above described media, in a 125 mL Erlenmeyer flask, mixed via a magnetic stir bar. Culture conditions were constant 230 µmol m-2 s-1 (cool white LED), 2% $CO_2$, and 33° C. Optical density at 750 nm was measured with a TECAN M plex microplate reader, using standard 1 cm pathlength cuvettes. These cultures were also used to determine the concentration of mCherry in the supernatant (described below).

To determine the concentration of mCherry in the supernatant, purified mCherry protein was purchased (BioVision) and used as a standard. Lyophilized mCherry protein was resuspended in water, and the concentration determined by Beer's Law, using the absorbance at 587 nm, an extinction coefficient of 72.00 M$^{-1}$cm$^{-1}$ and molecular weight of 28886 g/mol. This was then diluted (in NM2) to 0.019 mg/mL, and added (2, 4, 6 µL mCherry, 8, 6, 4 µL NM$^2$) to the supernatant (190 uL) of WIT cells to develop a standard curve. mCherry was quantified in the standard curve and secreting cell line with the above TECAN microplate reader at an excitation wavelength of 572 nm and emission of 610 nm, gain was set to 195.

Confocal fluorescence images were acquired using a Yokogawa CSU-X1 spinning disc confocal scan head attached to a Nikon Ti-E inverted microscope with 100×1.40 NA oil immersion objective. The algae were illuminated using the 561 nm laser line, and the resulting fluorescence observed using either a 625/50 band pass for the mCherry, or a 665 long pass filter to observe chlorophyll autofluorescence. An Andor 888 Ultra EMCCD was used to acquire the resulting fluorescence signal. ImageJ was utilized for post imaging processing.

The foregoing disclosure has been set forth merely to illustrate the invention and is not intended to be limiting.

We claim:

1. A novel photosynthetic protein secretion platform comprising a non-naturally occurring *Picochlorum renovo*, wherein the non-naturally occurring *Picochlorum renovo* comprises a secretory signal peptide that is SEQ ID NO: 2 or SEQ ID NO: 5 and expresses a transgenic protein of interest, and wherein the secretory signal peptide is expressed with a transgenic protein of interest.

2. A method for expressing a transgenic protein of interest in a photosynthetic protein secretion platform comprising the step of transforming a *Picochlorum renovo* with a gene encoding the transgenic protein of interest, wherein the *Picochlorum renovo* comprises a secretory signal peptide that is SEQ ID NO: 2 or SEQ ID NO: 5, and wherein the secretory signal peptide is expressed with a transgenic protein of interest.

* * * * *